(12) United States Patent
Falk et al.

(10) Patent No.: US 6,796,777 B2
(45) Date of Patent: Sep. 28, 2004

(54) LOW POWER ELECTROMAGNETIC PUMP

(75) Inventors: Theodore J. Falk, Clarence, NY (US); Norbert W. Frenz, Jr., Clarence, NY (US)

(73) Assignee: Wilson Greatbatch Technologies, Inc., Clarence, NY (US)

(*) Notice: Subject to any disclaimer, the term of this patent is extended or adjusted under 35 U.S.C. 154(b) by 0 days.

(21) Appl. No.: 10/291,130

(22) Filed: Nov. 8, 2002

(65) Prior Publication Data

US 2003/0086799 A1 May 8, 2003

Related U.S. Application Data

(60) Provisional application No. 60/338,075, filed on Nov. 8, 2001, and provisional application No. 60/347,162, filed on Jan. 9, 2002.

(51) Int. Cl.[7] ............................ F04B 17/04; F04B 35/00; H02K 33/00; H01F 7/06
(52) U.S. Cl. ......................... 417/417; 417/53; 417/415; 417/416; 310/23; 29/602.1
(58) Field of Search ................. 417/53, 417, 569, 417/415, 416; 92/130 R, 135; 29/602.1; 310/23, 15

(56) References Cited

U.S. PATENT DOCUMENTS

| | | | | |
|---|---|---|---|---|
| 2,043,270 A | * | 6/1936 | Twiss ......................... 417/44.8 |
| 3,153,735 A | * | 10/1964 | Branagan et al. ............. 310/15 |
| 4,376,618 A | * | 3/1983 | Toyoda et al. ............... 417/417 |
| 4,636,150 A | | 1/1987 | Falk et al. |
| 5,289,627 A | * | 3/1994 | Cerny et al. ................ 29/602.1 |
| 5,797,733 A | * | 8/1998 | Falk et al. ................... 417/416 |
| 5,915,929 A | | 6/1999 | Falk et al. |
| 6,193,477 B1 | | 2/2001 | Falk et al. |
| 6,227,818 B1 | * | 5/2001 | Falk et al. ................... 417/415 |
| 6,264,439 B1 | * | 7/2001 | Falk et al. ................... 417/417 |
| 6,454,548 B2 | | 9/2002 | Falk et al. |
| 2001/0043873 A1 | | 11/2001 | Hironaka et al. |

* cited by examiner

*Primary Examiner*—Justine R. Yu
*Assistant Examiner*—Timothy P. Solak
(74) *Attorney, Agent, or Firm*—Hodgson Russ LLP

(57) ABSTRACT

An electromagnetic pump comprising an armature comprising a pole portion joined to a plunger portion, wherein the plunger portion comprises a one-piece structure including shaft portions of increasing diameters and a head portion comprising a diameter greater than the shaft portions, the plunger portion and a pole portion located internal to the pump housing for magnetic attraction by an electromagnet means. A retainer element is joined with the plunger portion and a main spring urges on the retainer element to move the plunger thus allowing for a return stoke of the plunger as the pump cycles. Guiding of the armature is performed exclusively by a cooperating relationship between the armature plunger portion and an adjacent portion at the pump housing.

33 Claims, 12 Drawing Sheets

LOW POWER ELECTROMAGNETIC PUMP

CROSS REFERENCE TO RELATED APPLICATIONS

Applicants claim priority based on U.S. Provisional Patent Application entitled LOW POWER ELECTROMAGNETIC PUMP, bearing Serial No. 60/338,075 and filed in the United States Patent and Trademark Office on Nov. 8, 2001, the entire contents of which are hereby incorporated by reference. Applicants also claim priority based on U.S. Provisional Patent Application entitled LOW POWER ELECTROMAGNETIC PUMP, bearing Serial No. 60/347,162 and filed in the United States Patent and Trademark Office on Jan. 9, 2002, the entire contents of which are hereby incorporated by reference.

FIELD OF THE INVENTION

The present invention relates to the field of electromagnetic pumps, and further relates to the use of low power electromagnetic pumps for use in implantable medical device applications.

BACKGROUND

Presently, small pumps are used to pump liquids such as medicines, drugs, insulin, chemotherapy liquids, and other life critical drugs to a patient. These pumps are sometimes required to be quite small given the fact that they oftentimes will be implanted into the patient's body. If they are implanted, it is desirable that the pump have a low power requirement so that the battery which powers the electromagnetic pump has a long life. A battery with a long working life is therefore desirable for use in such instances.

In the past, the low power electromagnetic pumps available in and used for the purposes described above were complex mechanisms. Complex not only in the manner in which they functioned, but also complex in the manner in which they were made. Indeed, a drawback associated with the prior pumps is that they are made of a plurality of complex parts. These parts are difficult to manufacture due to the size requirements of the pump. Take for example the armature of a typical prior pump. In the past, the armature was made of a plurality of complex delicate parts, all of which had to be arranged inside the pump housing in an equally delicate and complicated process. Positioning and aligning these parts in the pump housing was a difficult and tedious task. Also, these pumps required excessive amounts of time to manufacture the intricate components, meaning mass production of the components was simply not a viable option.

A requirement of such a pump is that it have a low power drain, since the pump will in many applications be powered by an implanted battery. Another requirement is that the pump be compatible with the drugs/fluids being pumped. Other requirements are that the pump have a simplified structure and method of assembly while simultaneously having improved performance. More requirements are that the pump operates in a manner preventing damage to fragile drugs, such as insulin, and that moving parts of the pump be resistant to wear, thus prolonging the pump's useful working life.

It would therefore be desirable to provide an electromagnetically operated pump which is safe, reliable, small in size, light in weight, operates with low power requirements, and which is compatible with drugs, such as insulin, or other liquids to be pumped, and which has a relatively simple structure and method of assembly and improved performance. It would also be desirable to provide a pump having parts able to be mass produced efficiently and without difficulty, and it would be useful if the actual assembly of the pump was simplified such that assembly time is reduced. This would result in an reliable pump that can be mass produced at lower production costs, a pump that operates in a manner preventing damage to fragile drugs such as insulin, and a pump that is resistant to the detrimental effects of the drugs, insulin, or other fluids being pumped, and which has wear resistant moving parts.

SUMMARY

The low power electromagnetic pump operates at an extremely low power, and it may be used in implantable drug delivery systems, although the principles of this invention can be variously applied. That is, the low power electromagnetic pump also may be employed in applications external to a patient's body.

The present invention provides an electromagnetic pump comprising a housing having an interior fluid containing region including a fluid receiving chamber in communication with an inlet, a fluid output chamber in fluid communication with an outlet, and a check valve means operatively associated with the fluid containing region for allowing fluid flow in a direction from the inlet toward the outlet and blocking fluid flow in a direction from the outlet to the inlet. Electromagnet means are carried by the housing and located external to the fluid containing region, and barrier means of fluid impervious material isolates the electromagnet means from the fluid chambers. An armature is positioned in the housing and comprises a pole portion located for magnetic attraction by the electromagnet means and has a plunger portion joined with and extending from the pole portion. The armature is supported in the housing for movement from a rest position through a forward pumping stroke when attracted by the energized electromagnet means to force fluid from the output chamber through the outlet, and for movement in an opposite direction through a return stroke back to the rest position when the electromagnet is de-energized.

The armature comprises a pole face portion and a plunger portion, with the plunger portion comprising and a first shaft portion, a second shaft portion of greater diameter than the first shaft portion, a third shaft portion of greater diameter than the second shaft portion, and a head portion of greater diameter than the third shaft portion. The armature plunger portion can be machined from a piece of plunger stock, thus providing for a one piece plunger portion. The plunger portion may comprise, for example titanium, titanium alloys, metals, and biocompatible materials. An inner weld ring joins the head portion with the pole portion. The pole portion is encased in a in a titanium shell and holds a body of magnetic material. A retainer element is joined to the second shaft portion, and the main spring is captured between the retainer element and a retainer plate. The main spring is for storing energy during a forward pumping stroke and releasing energy during the return stroke. Guiding of the armature as it reciprocates is provided by the cooperation between the outer surface of the first plunger section and the adjacent housing of the pump.

DETAILED DESCRIPTION OF THE INVENTION

The present invention is for a low power electromagnetic pump of the type shown in, for example, U.S. Pat. No. 6,227,818 to Falk et al. for a Low Power Electromagnetic Pump issued May 8, 2001; and U.S. Pat. No. 6,264,439 to Falk et al. for a Low Power Electromagnetic Pump issued Jul. 24, 2001, the disclosures of which are hereby incorporated by reference.

Figure 1:
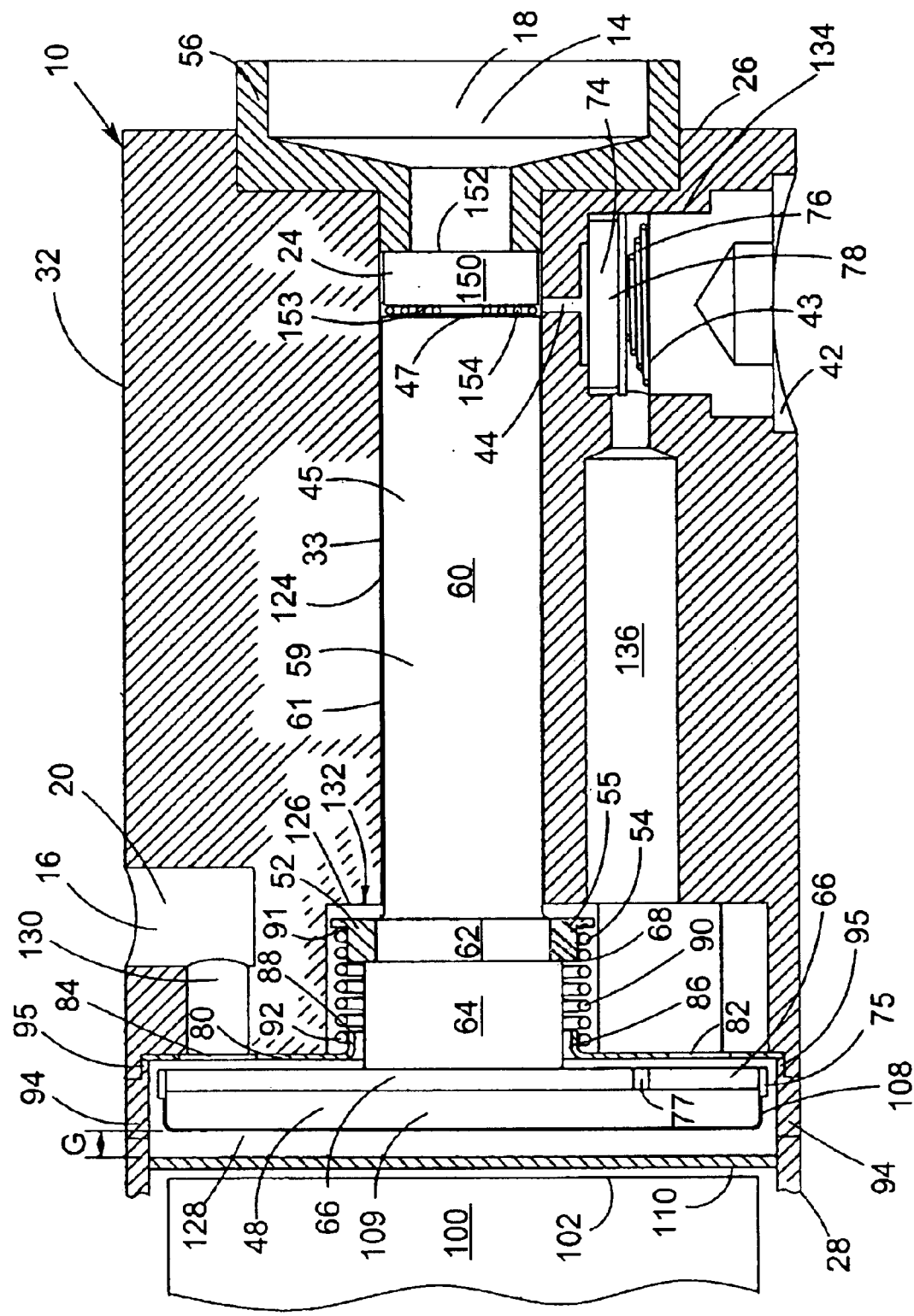
FIG. 1 is a longitudinal fragmentary sectional view of the pump.

FIG. 1 shows a longitudinal sectional view of the pump 10. The pump 10 comprises a cylindrical body or housing 32, as shown, but in other embodiments the housing 32 may comprise other shapes, for example, rectangular and elliptical. The housing 32 is generally hollow, and defines a fluid receiving chamber 14 and a fluid output chamber 16 in fluid communication with one another in a manner to be described presently. There is an inlet port generally designated 18 in fluid communication with the fluid receiving chamber 14 and adapted to be connected in the fluid handling circuit containing pump 10. There is also an outlet port 20 in fluid communication with the fluid output chamber 16 and adapted to be connected in the fluid circuit 34. Inlet port 18 is adapted to be connected to a source or supply of fluid to be pumped, and outlet port 20 is adapted to be in fluid communication with a location to which fluid is to be pumped. There is also provided a means for check valving 24 (hereinafter check valve means 24) operatively associated with the fluid-containing region of pump 10 for allowing fluid flow in a direction from the inlet port 18 through outlet port 20 and blocking fluid flow in a direction from the outlet port 20 through the inlet port 18. The check valve means 24 are within the pump 10 and are associated with the pump armature 45 in a manner which will be described. In the fluid circuit in which the pump 10 is employed, fluid (for example insulin, drugs, medications, chemotherapy drugs, and life critical drugs) enters the inlet port 18, and is then pumped through the pump 10, and exits the pump 10 through the outlet port 20. FIG. 1 shows the pump 10 at rest, the pumping cycle to be described in detail presently.

Figure 11:
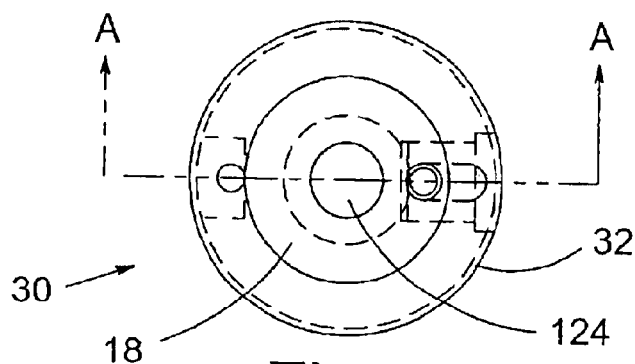
FIG. 11 is an elevational view of one end of the cylinder body of the pump of FIG. 1.
Figure 12:
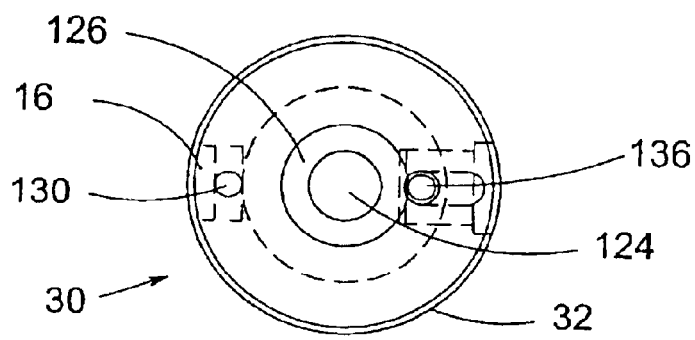
FIG. 12 is an elevational view of the opposite end of the cylinder body of FIG. 1.

The pump housing 32 defines a plurality of chambers in the pump 10. The chambers are shown in FIGS. 11–17, and for purposes of clarity, the internal components of the pump 10 are not shown in these figures. Turning to FIG. 11, shown therein view of the cylindrical housing 32. The housing 32 may also be embodied to comprise shapes other than cylindrical, for example rectangular, polygonal, elliptical, and combinations thereof. FIG. 11 shows the fluid inlet port 18. FIG. 12 shows the armature shaft chamber 124 and the main spring retainer chamber 126, and bypass chamber 136. FIG. 14 shows an exploded side elevational cutaway view of the portion of the housing 32 in the vicinity of the bypass chamber 136.

Figure 13:
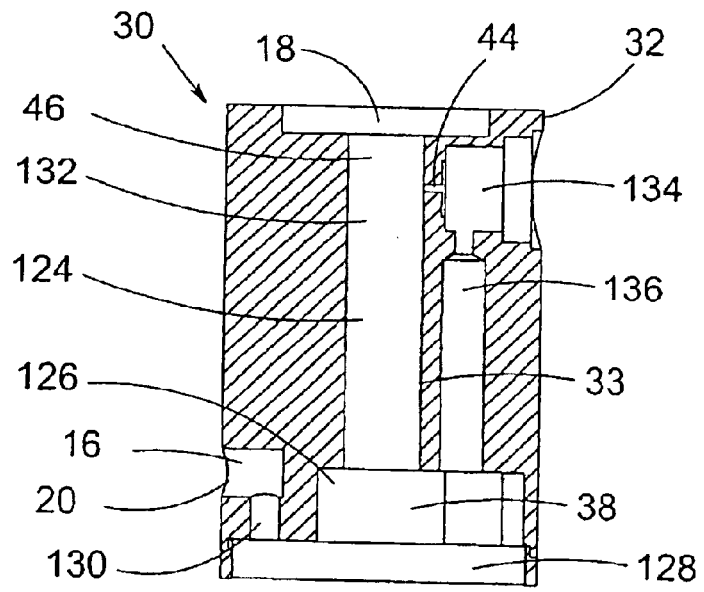
FIG. 13 is a longitudinal sectional view of the cylinder body taken about on line A—A in FIG. 11.
Figure 14:
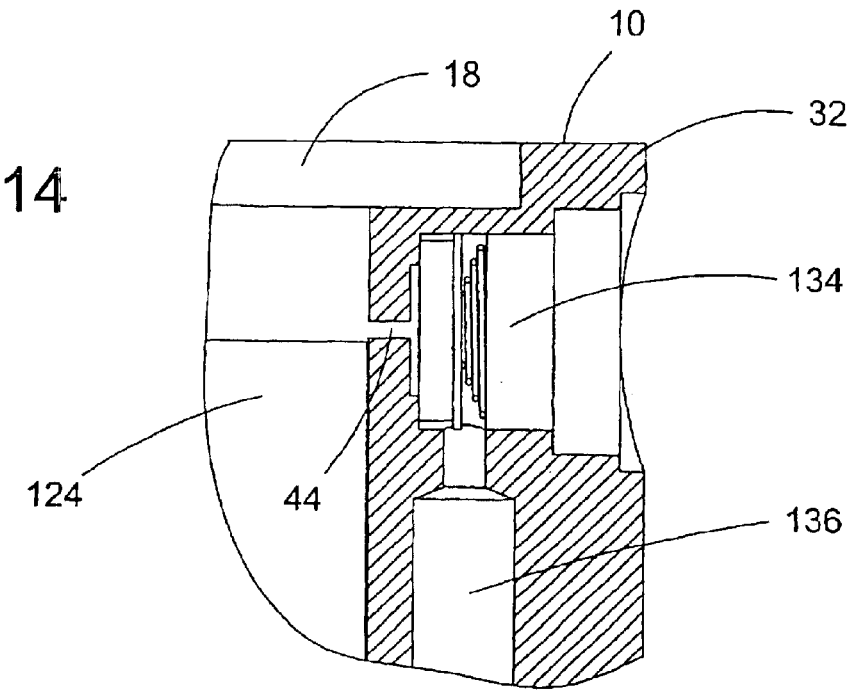
FIG. 14 is a enlarged view of the bypass section of the pump housing.

Turning to FIG. 13, the inlet port 18 is where incoming fluids enter the housing 32. For example, the inlet port 18 receives incoming drugs, medicines, insulin, and other fluids to be pumped by the pump 10. The inlet port 18 is in fluid communication with and leads to an armature shaft chamber 124 which is sized to accommodate the pump 10 armature 45 therein. The armature shaft chamber 124 leads to and is in fluid communication with a main spring retainer chamber 126 the width of which is greater than the width of the armature shaft chamber 124. The main spring retainer chamber 126 is in fluid communication with and leads to a pole button chamber 128, the width of the pole button chamber 128 being greater than the width of the main spring retainer chamber 126. The pole button chamber 128 is in fluid communication with and leads to a flow passage 130 which is in fluid communication with the fluid output chamber 16. An armature chamber 132 may be considered a combination of the armature shaft chamber 124, the main spring retainer chamber 126, and the pole button chamber 128, and it is for receiving the armature 45 therein.

The housing 32 further defines, between the armature shaft chamber 124 and pole button chamber 128 a fluid bypass path. A passage or orifice 44 defined in the housing 32 leads from the armature shaft chamber 124 to a plug chamber 134, the orifice 44 provides for fluid communication between the armature shaft chamber 124 and the plug chamber 134. The orifice 44 may be embodied to be an orifice of small diameter. The orifice 44 may be made by drilling, electric discharge machining, laser drilling, and by other known manners capable of producing an orifice 44 or passage of the correct size. The plug chamber 134 leads to and is in fluid communication with a bypass chamber 136.

Figure 15:
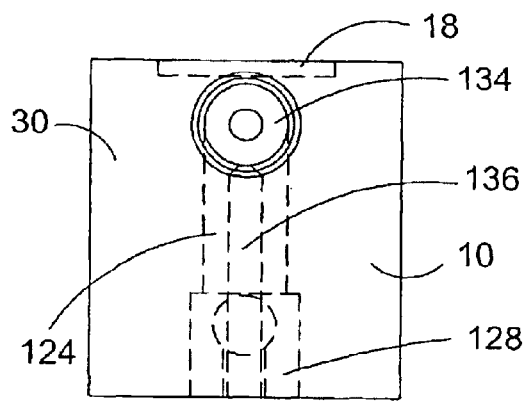
FIG. 15 is an elevational view of one side of the pump housing of FIG. 13 showing the bypass.
Figure 16:
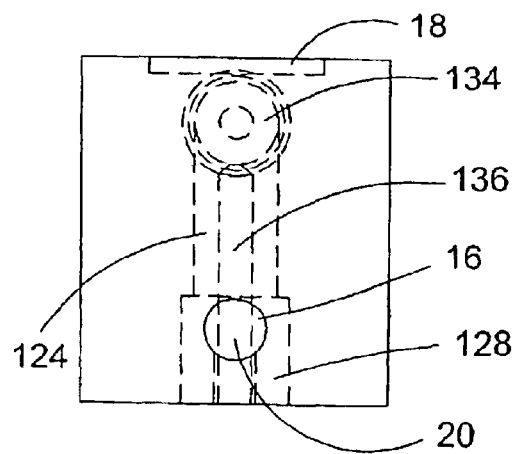
FIG. 16 is an elevational view of the opposite side of the of the pump housing shown in FIG. 13.
Figure 17:
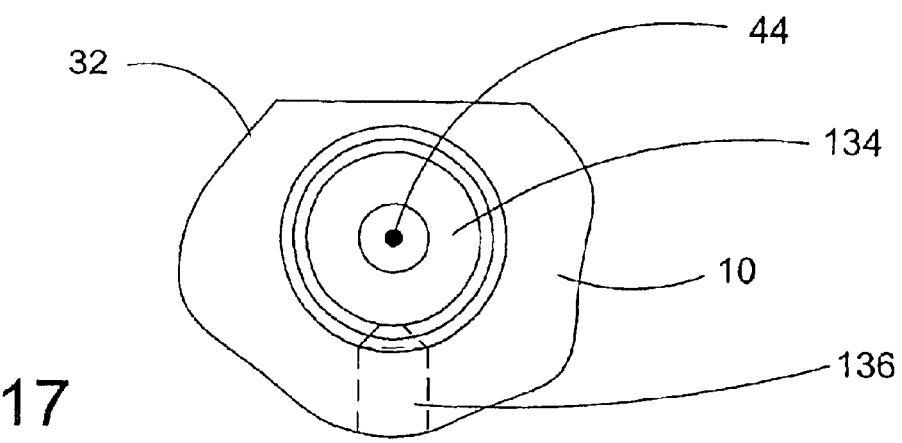
FIG. 17 is an enlarged end elevational view of the pump housing showing the bypass.

The bypass chamber 136 is in fluid communication with the pole button chamber 128. These chambers thus provide for a bypass path or passage in the pump 10. FIG. 14 is an expanded view of a portion of FIG. 13. FIGS. 15 and 16 are side elevational views of the cylindrical housing 32 shown in FIG. 13. FIG. 17 is an enlarged view of the bypass and plug chambers 136,134, respectively, as shown in FIG. 15.

Figure 6:
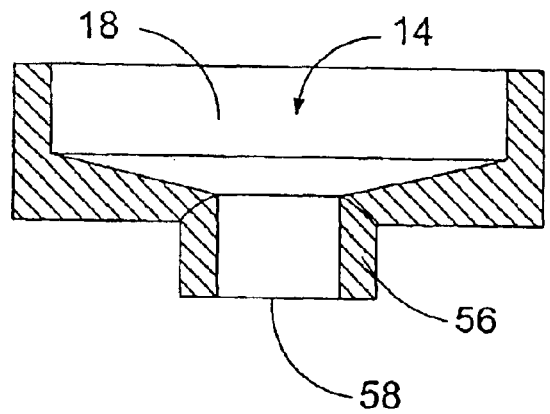
FIG. 6 is a side elevational sectional view of the seat ferrule of the pump of FIG. 1.
Figure 7:
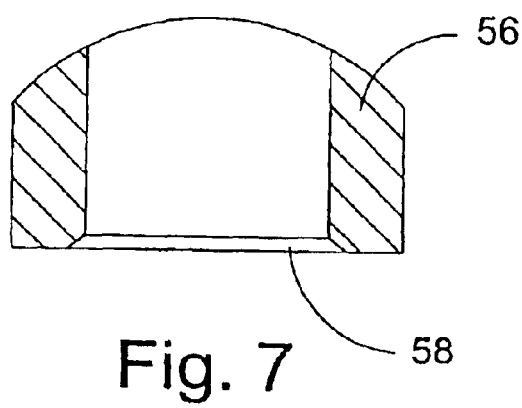
FIG. 7 is an enlarged sectional view of a portion of the seat ferrule of FIG. 6.
Figure 8:
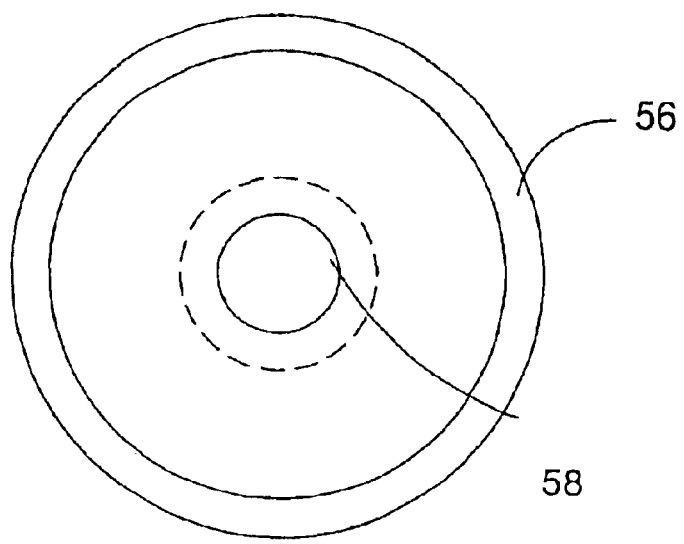
FIG. 8 is an end elevational view of the seat ferrule of FIG. 6.

The seat ferrule 56, shown in FIGS. 1, 6–8 respectively, is mounted to the housing 32 and defines the fluid receiving chamber 14 at the inlet port 18. FIG. 6 is a is side elevational cutaway view of the seat ferrule 56 and FIG. 7 is an enlarged view of a portion of FIG. 6 showing the chamfered cutout 58 in the seat ferrule 56. FIG. 8 is plan view of the seat ferrule 56. It is noted that upstream of the seat ferrule 56 there is a reservoir of fluid to be pumped (not shown in the figures).

Figure 2:
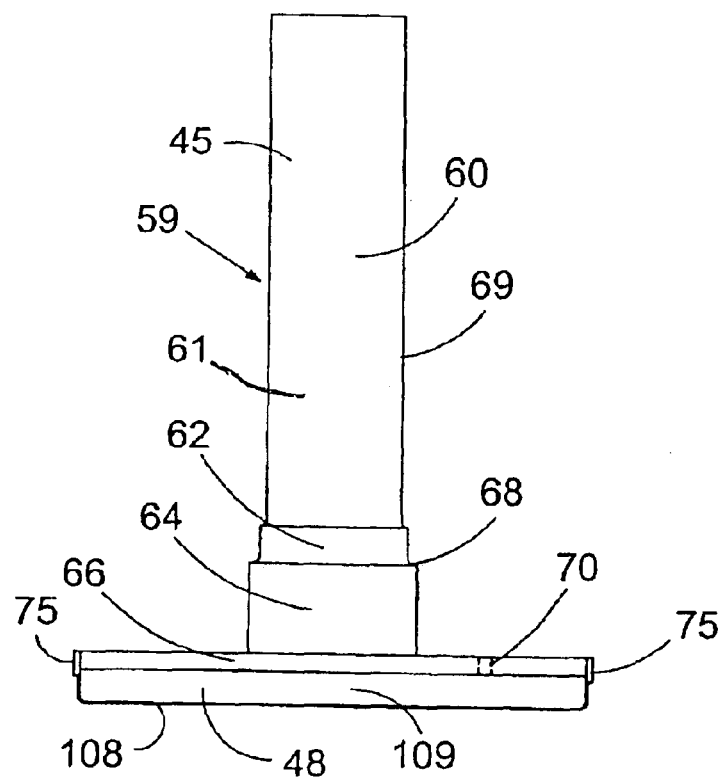
FIG. 2 is a side elevational view of the armature.
Figure 3:
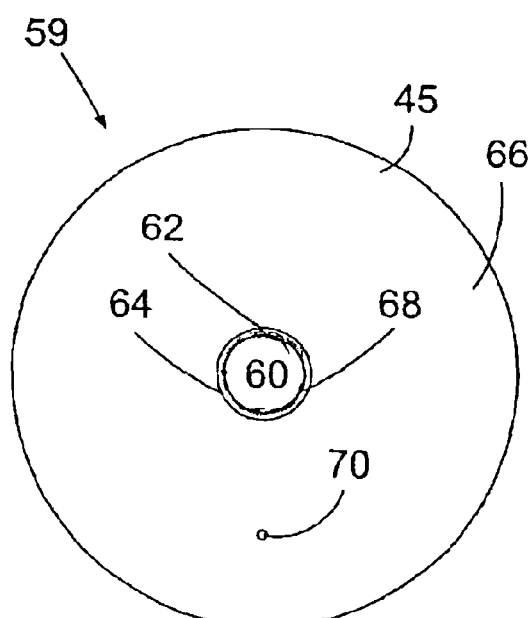
FIG. 3 is end elevational view of the armature.

Turning to FIG. 1, the pump armature 45 comprises a pole portion 48 and a plunger portion 59. The pole portion 48 is connected to the plunger portion 59 by an inner weld ring 75, as shown in FIGS. 1 and 2. The armature 45 plunger portion 59, shown in FIGS. 1–3, comprises a first shaft portion 60, a second shaft portion 62 of greater diameter than the first shaft portion 60, a third shaft portion 64 of greater diameter than the second shaft portion 62, and a head portion 66 comprising a diameter greater than the diameter of the third shaft portion 64. In an embodiment, the plunger portion 59 is machined and/or formed from a piece of plunger stock so that the finished machined plunger portion 59 is one piece, as opposed to a plurality of pieces. For example, the plunger portion 59 may be machined or otherwise formed from plunger stock into the first shaft portion 60, the second shaft portion 62, the third shaft portion 64, and the head portion 66, resulting in a plunger portion 59 which is one piece, as shown in FIG. 2. The plunger portion 59 may, for example, comprise: metals, titanium; titanium alloys; materials resistant to the effects of the fluids being pumped; and combinations thereof. The plunger 59 is preferably grade 5 bar stock titanium alloy. The head portion 66 defines a vacuum hole 70 for a purpose to be described presently. The pole portion 48 is attached to the head portion 66 by fitting the inner weld ring 75 about them and then joining them together.

The armature 45 pole portion 48 (or pole button) extends from the head portion 66. The pole portion 48 comprises a shell 108 which holds a magnetic material (a magnetic body 109) for attraction to the electromagnet means 100 (electromagnet 100). The shell 108, which may comprise titanium, titanium alloys, and other suitable materials, is joined to the head portion 66 by the inner weld ring 75. The pole portion 48 is encased to protect the body 109 against corrosion from insulin, drugs, medications, chemotherapy materials, life critical drugs, and other chemicals being pumped.

After placing the body 109 in the shell 108 and welding/joining the shell 108 to head portion 66, the pole portion 48 is sealed. First, a pin 77 is inserted into the vacuum hole 70 defined in the head portion 66. Then, a vacuum is applied such that a vacuum environment is created internal to the shell 108. Then, the pin 77 is welded/laser welded to the head portion 66, thus sealing the body 109 in a vacuum in the shell 108. Removal of all gasses from within the shell 108 causes the body 109 to be held firmly against the shell 108 and head portion 66. Such sealing prevents the body 109 from moving freely inside the shell 108, which prevents wear and tear on the pump 10 during pumping cycles. If the body were to freely move about the shell 108, the pump's 10 performance might decrease, and uncontrolled vibrations could occur inside the pump 10 as the armature 45 moves back and forth during pumping cycles.

Figure 24:
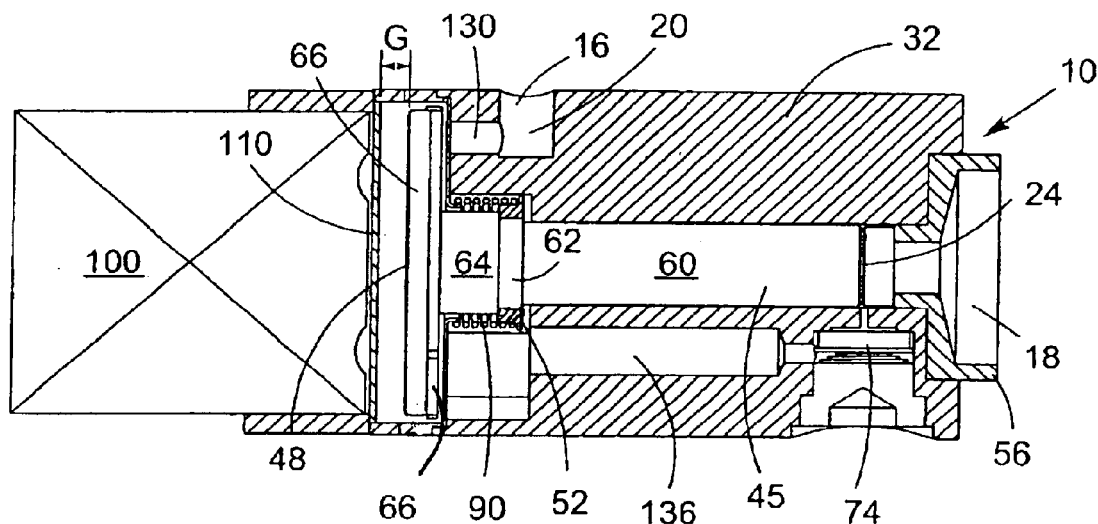
FIG. 24 is a diagrammatic view of the pump at rest.
Figure 25:
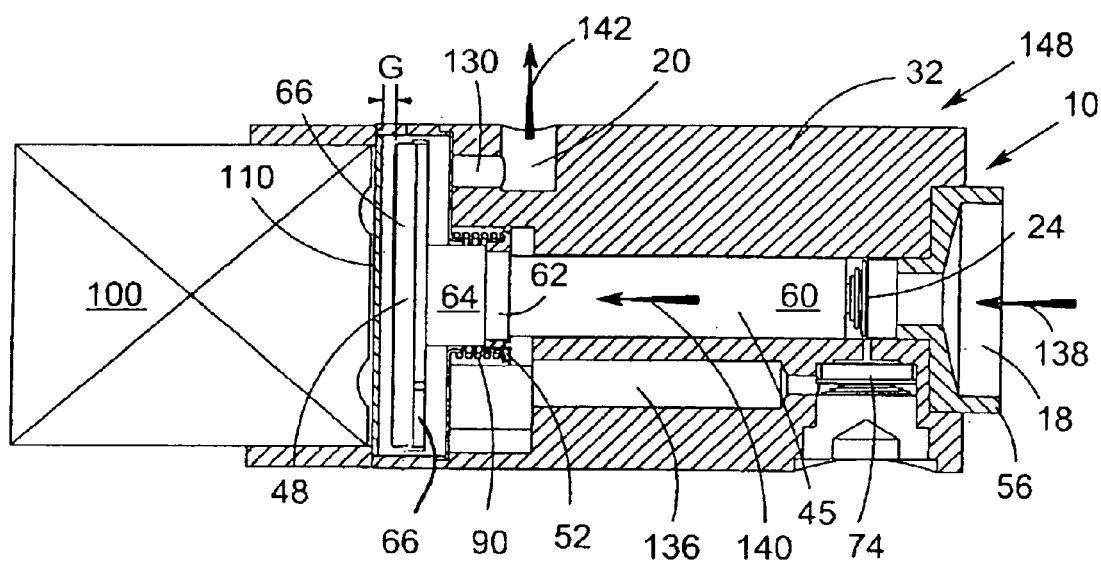
FIG. 25 is a diagrammatic view of the pump showing one stage of the forward stroke.

The main check valve means 24 is shown in FIG. 1, positioned in the armature shaft chamber 124. In a manner to be described presently, the main check valve means 24 allows fluid from an upstream location, for example a reservoir, to enter the pump 10 when the pump 10 is activated (the forward stroke of the pump 10). The check valve means 24 comprises a disc shaped body or seat 150 with one surface 152 contacting the seat ferrule 56 and the other side 153 contacting biasing spring 154. The biasing spring 154 biases against the seat 150 and the proximal end 47 of the armature 45. During a forward pumping stroke, to be described presently, the check valve means 24 opens allowing fluid from an upstream location, such as a reservoir, to enter the pump 10 through the inlet port 18 and flow into the fluid receiving chamber 14. Before the electromagnetic means 100 are activated, the pump 10 is in the deactivated state, shown in FIGS. 1 and 24. When the pump 10 activates, the pump armature 45 is drawn to the electromagnet means 100 as shown in FIG. 25 (this shows the forward stroke of the pump 10). The electromagnet means 100 is located at the one end 28 of the pump 10, opposite the end 26 of the pump 10. The electromagnetic means 100 is isolated from the fluid being pumped by a plate 110, the plate 110 may be embodied as a thin plate-like diaphragm. The plate 110 prevents the fluids being pumped from contacting the electromagnet 100 and its parts and components, or in other words, provides a fluid seal between the electromagnetic means 100 and the pump interior 38 (FIG. 13). The electromagnet means 100 serves to cyclically generate an electromagnetic field and is used to pull the armature 45 towards it when it is activated, which draws fluid into the pump 10. When the electromagnet means 100 is deactivated, the armature 45 returns to its at rest state (FIG. 1), and the check valve means 24 prevents any fluid flow from entering the fluid receiving chamber 14, or in other words, the check valve means 24 prevents backflow out of the pump 10.

Figure 9:
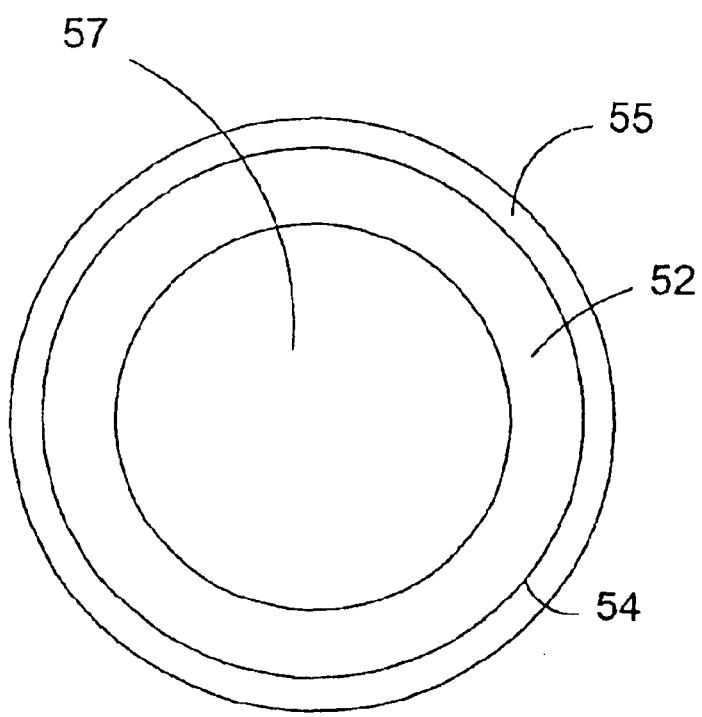
FIG. 9 is an end elevational view of the retainer element of the pump of FIG. 1.
Figure 10:
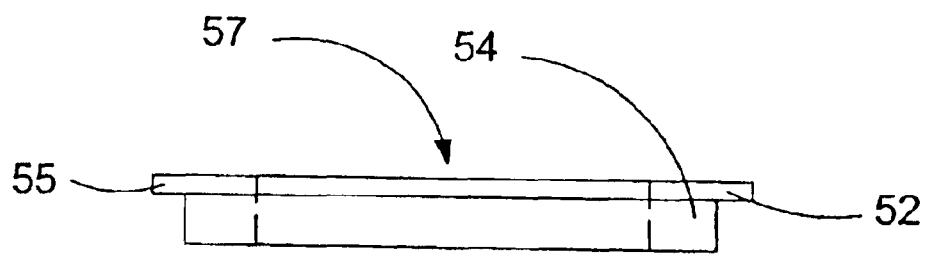
FIG. 10 is side elevational view of the retainer element of FIG. 9.

FIGS. 9 and 10 show end elevational and side elevational views of the retainer element 52. The retainer element 52 comprises an annular body 54 and a lip portion 55 that extends about its periphery, and defines a central opening or bore 57. The first and second shaft portions 60,62 of the armature 45 are fitted through the bore 57 of the retainer element 52. The retainer element 52 comes to rest at the shoulder 68 formed on the armature 45 where the where the second and third shaft portions 62,64, respectively, meet (FIG. 2). The retainer element 52 is joined to the second shaft portion 62 by welding/laser welding, and in other embodiments, the retainer element 52 may be joined to the second shaft portion 62 by a combination of welding/laser welding and friction fitting.

Figure 20:
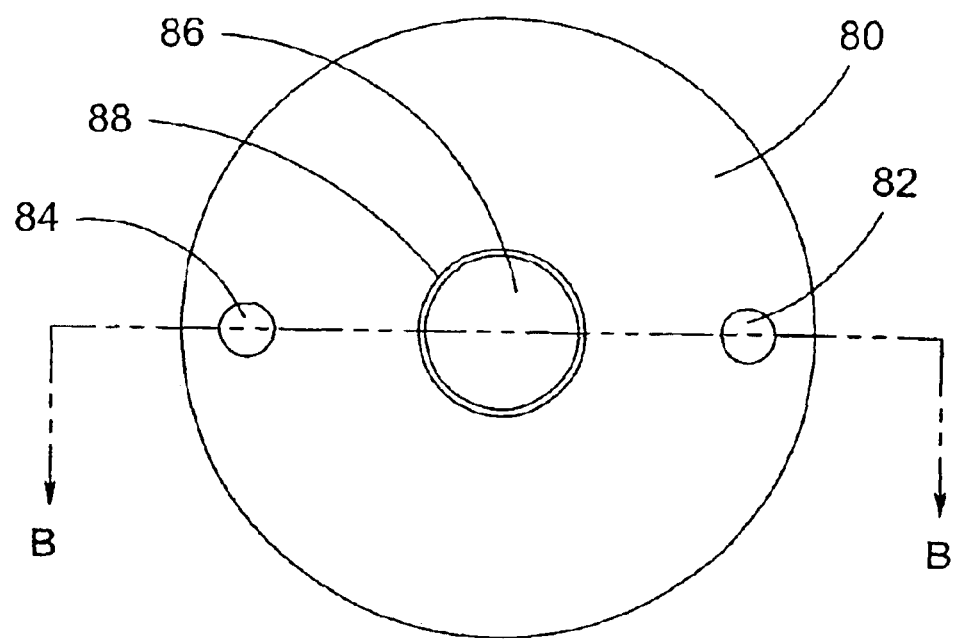
FIG. 20 is a top plan view of the spring retainer of the pump of FIG. 1.
Figure 21:
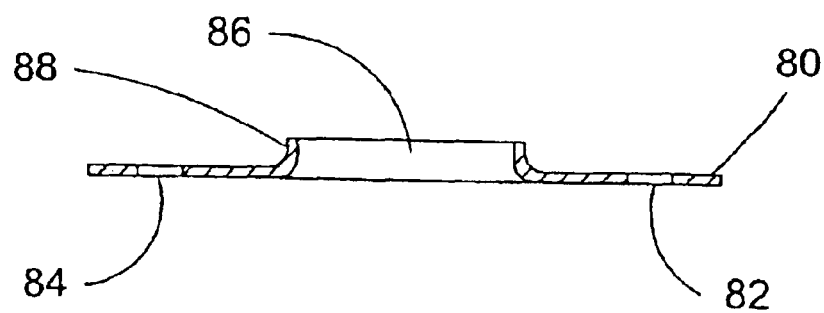
FIG. 21 is a sectional view of the spring retainer taken along cut line B—B of FIG. 20.
Figure 22:
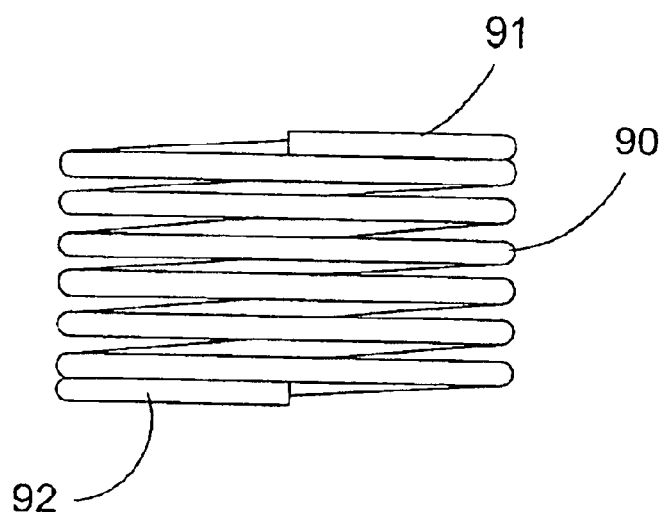
FIG. 22 is a side elevational view of the main spring of the pump of FIG. 1.
Figure 23:
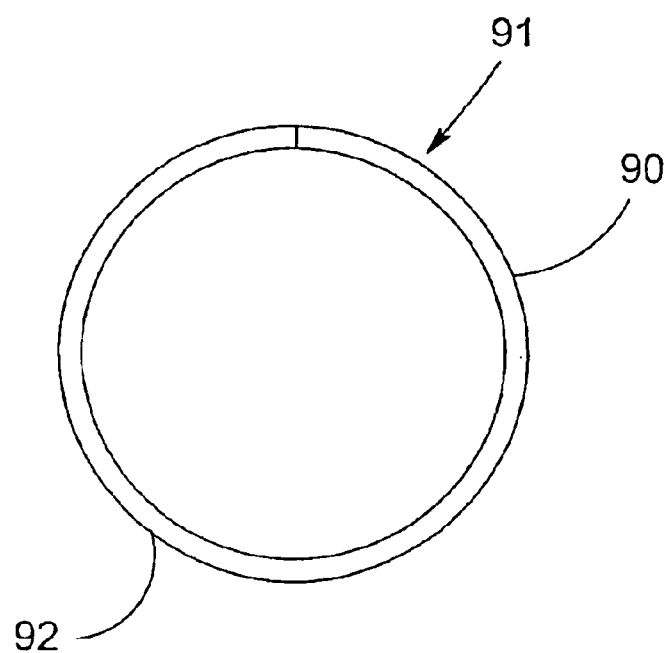
FIG. 23 is an top plan view of the main spring of FIG. 22.

FIG. 20 shows a top plan view of the retainer plate 80, and FIG. 21 shows a side sectional view of the retainer plate 80 taken along cut line B—B of FIG. 20. The retainer plate 80 defines a bypass fluid chamber opening 82 and an outlet opening 84, and a central opening 86. The central opening 86 is sized to receive the third plunger shaft portion 64 therein, as shown in FIG. 1. The retainer plate 80 also comprises an annular flange 88 surrounding the central opening 86. FIGS. 22 and 23 are side elevational and plan views of the main spring 90, also shown in FIG. 1. When the pump is assembled, as shown in FIG. 1, one end 91 of the main spring 90 abuts the lip portion 55 of the retainer element 52, and the opposite end 92 of the main spring 90 abuts against the annular flange 88 of the retainer plate 80.

Figure 18:
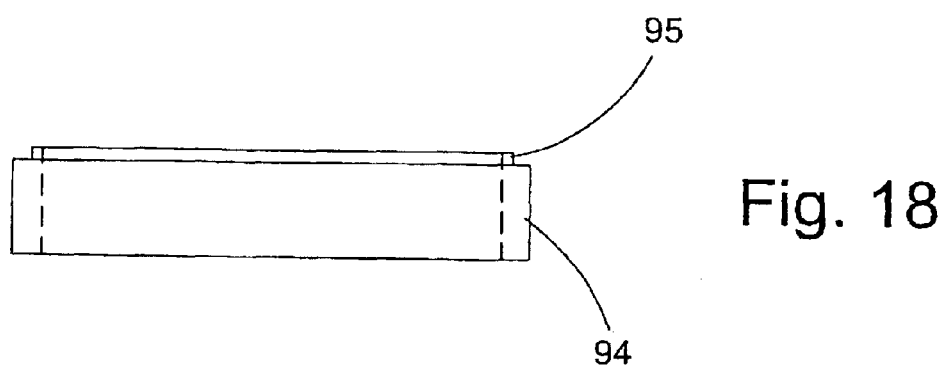
FIG. 18 is a side elevational view of the outer weld ring.
Figure 19:
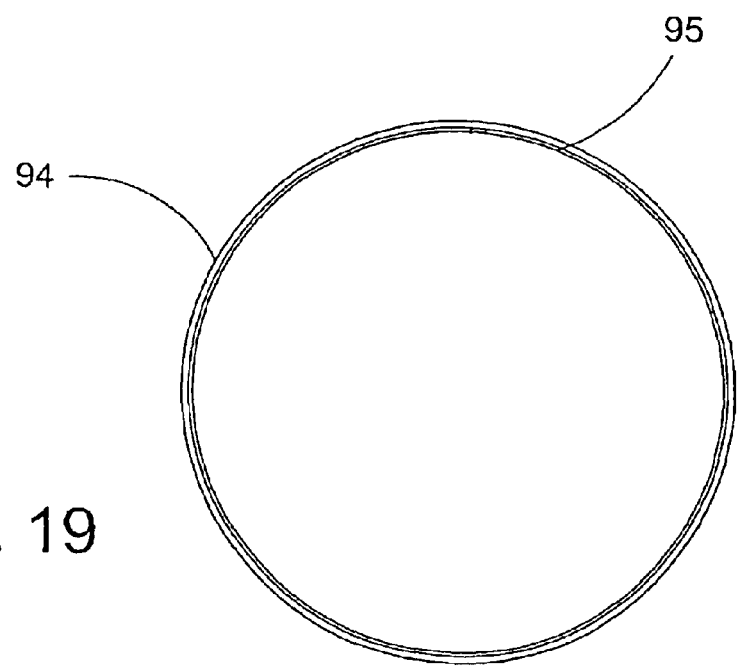
FIG. 19 is a an end view of the outer weld ring.

FIG. 18 is a side elevational view of the outer weld ring 94 of the pump 10 of FIG. 1, and FIG. 19 is an end view of the outer weld ring 94. The outer weld ring 94 further comprises an annular support protrusion or lip 95. The support protrusion 95 supports the retainer plate 80, as shown in FIG. 1. The retainer plate 80 is positioned between the housing 32 and the support protrusion 95, and becomes trapped therebetween upon welding the outer weld ring 94. This prevents the movement of the retainer plate 80 as the pump 10 cycles. Due to this configuration, the retainer plate 80 itself need not be welded.

The electromagnet means 100 is carried by the housing 32 and is external to the fluid containing region of the housing 32. The electromagnet 100 may comprise a core wrapped in a coil and is capable of rapidly energizing and de-energizing to create a magnetic field. This magnetic field then attracts the pole portion 48 of the armature 45. When the pole portion 48 is attracted, the armature 45 compresses the main spring 90 as it moves towards the electromagnet 100. At substantially the same time fluid is drawn into the pump 10. When the electromagnet 100 deactivates (de-energizes) the main spring 90 expands and applies force on the retainer element 52 which moves the armature 45 back to its at rest position in the pump 10 (FIG. 1).

Figure 4:
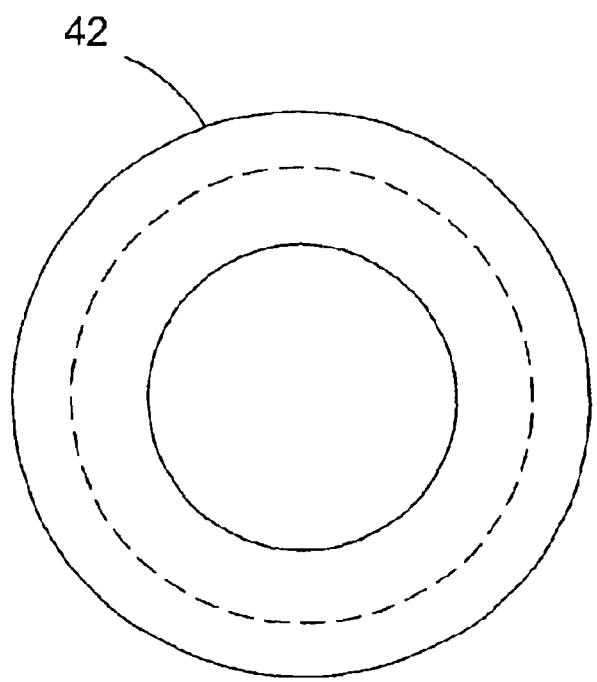
FIG. 4 is an end elevational view of the plug of the pump of FIG. 1.
Figure 5:
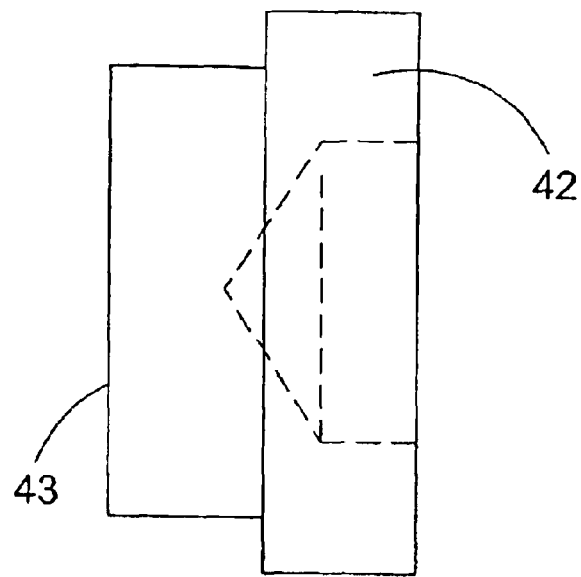
FIG. 5 is a side elevational view of the plug of FIG. 4.

Continuing with the structure of the pump 10, FIGS. 1, and 4–5, show end and side elevational views of the plug 42 which is mounted to the housing 32 in the plug chamber 134 (FIG. 13). The means for bypass check valving 74 (bypass check valve means) 74 is positioned internal to the housing 32, between the orifice 44 and the bypass chamber 136. Spring 76 is located between check valve element 78 and the end 43 of the plug 42. The bypass check valve means 74 controls fluid communication between the orifice 44 and bypass fluid chamber 136. That is, during the return stroke when the electromagnet 100 deactivates and the armature 45 returns to its starting position (rest position) shown in FIG. 1, the bypass check valve means 74 opens. Fluid from the armature shaft chamber 124 moves through the orifice 44, forces on element 78 and opens the bypass check valve means 74. The fluid then moves into the bypass chamber 136.

Assembly of the Armature and Movement of the Armature

Assembly of the armature 45 and installation thereof into the pump 10 housing 32 is accomplished with relative ease. The following acts are performed prior to insertion of the armature 45 into the above described plurality of chambers in the housing 32. First, the armature 45 is machined to take on the shape of the first shaft portion 60, second shaft portion 62, third shaft portion 64, and the head portion 66. The pole portion 48 is joined with head portion 66 of the armature 45 by welding the inner weld ring 75 to the titanium shell 108, as previously described.

Then the first, second, and third shaft portions 60,62, and 64, respectively, can be moved through the central opening 86 in the spring retainer plate 80 and through the main spring 90. Then, the first and second shaft portions 60,62, respectively, are moved through the retainer element 52 until the retainer element 52 contacts shoulder 68 (FIG. 2). Then, the retainer element 52 can be joined, welded/laser welded, or pressure fitted and welded/laser welded to the second shaft portion 62. At this point the main spring 90 is captured between the retainer element 52 and retainer plate 80. Of course, the retainer plate 80 is aligned such that its outlet opening 84 allows for fluid communication between the pole button chamber 128 and the flow passage 130, and the retainer plate 80 is further aligned such that its bypass chamber opening 82 allows for fluid communication between the pole button chamber 128 and the bypass chamber 136. The armature 45 is then inserted into the previously described armature shaft chamber 124 defined in the housing 32, with the end 47 of the armature 45 inserted first.

After the armature 45 is inserted into the armature shaft chamber 124, the outer weld ring 94 can be moved into the housing 32 around the retainer plate 80, until the outer weld ring 94 support protrusion 95 and retainer plate 80 contact. The outer weld ring 94 then can be welded/laser welded to the housing 32. The retainer plate 80 does not need to be welded to the housing 32, as it is trapped between the housing 32 and the support protrusion 95 which extends from the outer weld ring 94.

Figure 26:
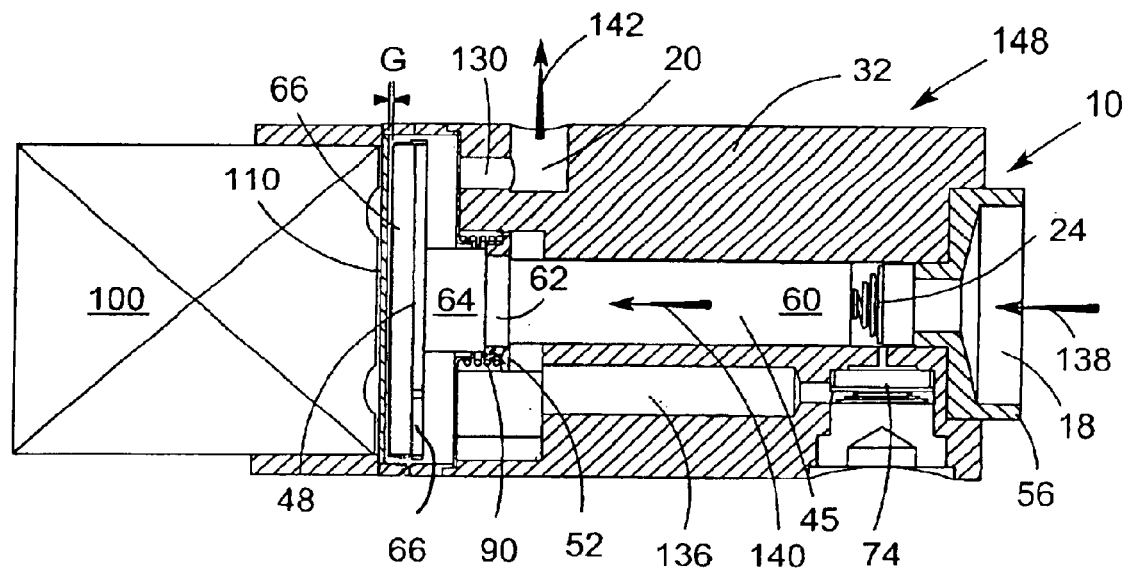
FIG. 26 is a diagrammatic view of the pump showing one stage of the forward stroke.
Figure 27:
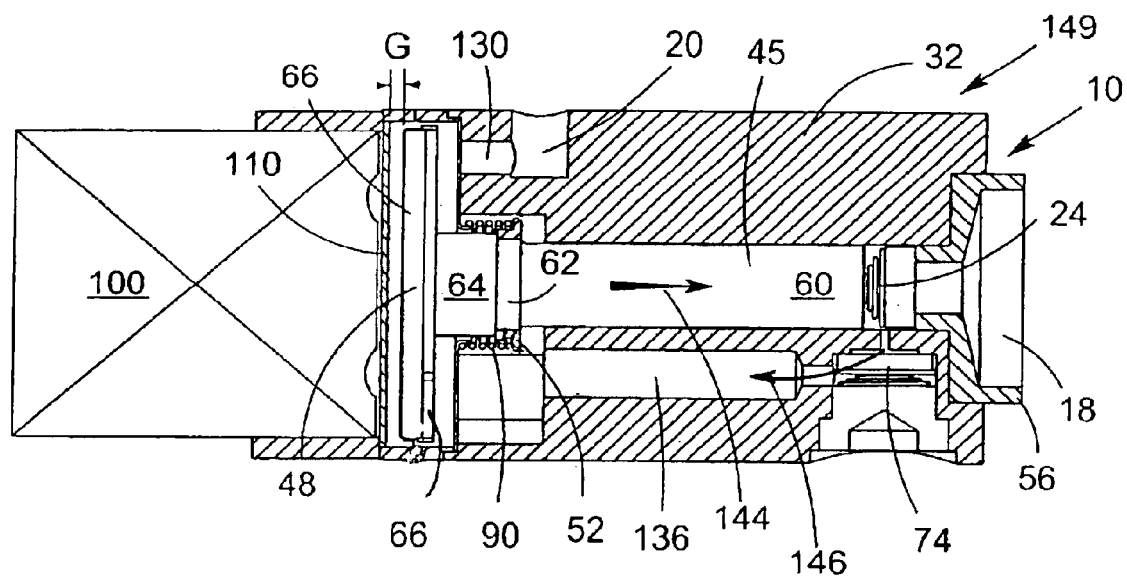
FIG. 27 is a diagrammatic view of the pump showing the return stroke.

The armature 45, as shown in FIG. 1, reciprocates as follows:

a) when the electromagnet means 100 is deactivated, the pump 10 appears as shown in FIG. 1 with the armature 45 in the at rest position;

b) a means defining a magnetic circuit comprising the electromagnet means 100 and the armature 45 and a gap (designated G in FIG. 1 and diagrammatic FIGS. 24–27) between the pole portion 48 of the armature 45 and the electromagnet means 100 moves the armature 45 toward the electromagnet means 100 to close the gap designated G in response to electrical energization of said electromagnet means 100;

c) during this forward stroke designated 148 in FIGS. 25 and 26, the pole portion 48 is drawn to the electromagnet 100, the check valve 24 opens and fluid enters the pump 10, and fluid also exits the pump through the outlet port 20;

d) as the forward stroke 148 continues, the main spring 90 compress between the retainer element 52 (this is welded to the second plunger section 62) and the retainer plate 80 (this plate is trapped between the outer weld ring 94 support protrusion 95 and the housing 32) and the armature 45 moves toward the electromagnet 100; and e) when the electromagnet 100 deactivates the gap G is substantially closed, and the means defining the magnet circuit no longer influences the armature 45, and the main spring 90 releases its stored energy, expands, and forces on the retainer element 52, causing the armature 45 to return to its at rest position, this being the return stroke designated 149 in FIG. 27.

This is thus the movement of the armature 45 when it is positioned inside the armature shaft chamber 124 defined in the housing 32. It is noted that guiding of the armature 45 is provided by cooperation between the outer surface 61 (FIGS. 1 and 2) of the first shaft portion 60 and the adjacent housing 33.

Operation of the Pump

With the parts of the pump 10 assembled as described above, the pump 10 is ready to begin the pumping cycle. Reference is made to diagrammatic FIGS. 24–27, which show the pumping process. FIGS. 1 and 24 are sectional side elevational view of the pump 10 at rest. As shown, the armature 45 is in its rest position. No fluid flow passes through the inlet port 18, due to the check valve means 24 blocking fluid flow through the pump 10.

Next, the electromagnet 100 is energized which creates a magnetic field in the vicinity of the plate barrier 110 (FIG. 25). The armature 45 pole portion 48 is drawn towards the barrier 110. As this happens, the movement of the armature 45 is to the left (as shown in FIGS. 25 and 26). That is, the armature 45 moves in the direction indicated by the arrow designated 140 in diagrammatic FIGS. 25 and 26. This is generally called the forward pumping stroke 148 of the pump 10. The main spring 90 is compressed between the lip portion 55 of the retainer element 52 and the retainer plate 80 during the forward pumping stroke 148.

As shown in FIG. 25, during the forward pumping stroke 148, fluid to be pumped enters the pump 10 at the inlet port 18, as shown by the fluid inflow arrow designated 138 in FIGS. 25 and 26. This happens because as the armature 45 moves towards the electromagnet 100, the check valve 24 opens and the fluid to be pumped enters armature shaft chamber 124. Fluid begins to move through the fluid circuit. Also during the forward pumping stroke 148, fluid exits the pump 10 through the passage 130 and out the outlet port 20, which is indicated by outflow arrow 142 in FIGS. 25 and 26. From that point, the fluid may pass through a catheter or the like into a patient's body or other desired location. During the forward pumping stroke 148 fluid does not pass through the bypass check valve 74, as the bypass check valve 74 remains closed.

The armature 45 moves the distance of its stroke determined by the time when the electromagnet means 100 deactivates (it de-energizes) and the return stroke 149 follows. The armature 45 moves in the direction of the arrow designated 144 to its rest position as shown in diagrammatic FIG. 27. This movement is accomplished when main spring 90 releases its stored energy, which moves armature 45 toward check valve 24. The check valve 24 closes during the return stroke, thus preventing any backflow of fluid out of the pump 10.

As this occurs, the fluid between the check valve 24 and the end 47 of the armature 45 becomes pressurized. This fluid makes its way through the orifice 44 and forces on check valve element 78 of the bypass check valve 74. In the region of the housing 32 where the orifice 44 located, the housing 32 is of sufficient dimension to provide the necessary strength in order to handle any stresses encountered in the region on account of incoming fluid passing through the orifice 44 encountered during the return stroke 149. The passage defining the orifice 44 is of such a length that the surrounding housing 32 has sufficient strength. The bypass hole or orifice 44 in the housing 32 may be made by laser drilling, electric discharge machining, drilling, and other manners known to producing orifices 44 of correct size. The bypass check valve 74 opens, and fluid moves through the orifice 44, past the bypass check valve 74, and into bypass chamber 136. The arrow 146 designates the return fluid flow as shown in diagrammatic FIG. 27. Since check valve 24 is closed during the return stoke 149, no fluid exits the pump 10 through the inlet port 18 during the return stroke 149.

The above described cycle typically is repeated at predetermined intervals in order to deliver the prescribed amount of drugs, medicine, insulin, chemotherapy, pain management drugs, and chemicals to the patient. Also, since the pump 10 may comprise titanium, titanium alloys, and other non-corrosive materials, it is well suited for these applications.

The pump 10 can be used in combination with other implantable medical devices, and in combination with primary cell batteries, for example lithium batteries. It can also be used in combination with rechargeable power sources, for example rechargeable battery cells. It also can be used with capacitors rechargeable by radio frequency energy or other means. Another use for the present pump 10 is in life critical situations as a means to deliver drugs, medicines, pain killers, wherein the pump 10 is located external to the patient.

The low power electromagnetic pump 10 (FIG. 1) thus achieves results which overcome drawbacks associated with the prior art. One of these results is that pump 10 is able to be mass produced, due in part to the configuration of its components. Contributing to this is another result achieved by the pump 10 in that the alignment of the armature 45 plunger portion 59 is not problematic, as the plunger is a single piece which is inserted into the pump 10 during assembly, rather than a plurality of pieces that must be assembled while located internal to the pump, and this thus alleviates fixturing problems. For example, first, second, third shaft portion 60, 62, 64, respectively, and head portion 66 may be machined or otherwise formed from a single piece of plunger stock 67. Yet another result achieved by the pump 10 is that the retainer element 52 is joined with the plunger armature 45, thereby facilitating ease of assembly. In addition, the body 54 and lip portion 55 of the retainer element 52 are combined into a single part thereby contributing to the easy assembly of the pump.

Guiding of armature 45 is also facilitated, because the armature 45 is guided by a cooperating relationship between the first shaft portion 60 outer surface 61 and the adjacent housing inner surface 33 (shown in FIG. 1) as the armature 45 reciprocates. In this connection, the length of plunger section 60 is longer than in pumps of this type heretofore available. This, in turn, enables the clearance between the outer surface 61 of the first shaft portion 60 and the adjacent housing inner surface 33 to be increased. In particular, this allows an increase in the range of the amounts of such clearance without an undesirable fluid leakage toward check valve 24 during the forward pumping stroke 148.

The increase in the allowable clearance between the first plunger section 60 and the adjacent housing inner surface 33 arises from the dependence of the viscous flow rate of fluid through a channel upon the length and height of the channel. For a two dimensional channel having a width W and a length L, with a pressure difference from end to end, P, the steady state viscous volume flow rate is proportional the height H, of the channel to the third power and to the inverse of its length L. Thus, given the length L of the channel is increased by a given factor F then the height H of the channel (in this case the difference between the radius of the housing 32 inner surface 33 and the outer surface 61 of the first plunger portion 60) may be increased may be increased by the factor F to the ⅓ power without increasing the rate of leakage of fluid past the plunger portion 59. The actual leak rate which can be tolerated in a given pump design depends upon a number of factors including the accuracy required by the pump, the length of the plunger stroke, the diameter of the plunger, the pressure increase across the pump, the compliance of any accumulators upstream and downstream of the pump, size of orifices in the flow path, and the dimensions of rigid tubing attached to the pump. The foregoing increased clearance provides the advantages of ease of manufacture and assembly and reduced wear during operation.

It will be appreciated by those skilled in the art that while the low power electromagnetic pump has been described in connection with particular embodiments and examples, the low power electromagnetic pump is not necessarily so limited and that other examples, uses, modifications, and departures from the embodiments, examples, and uses may be made without departing from the low power electromagnetic pump. All these embodiments are intended to be within the scope and spirit of the appended claims.

What is claimed:
1. An electromagnetic pump comprising:
   a) a housing defining an interior fluid containing region comprising a fluid receiving chamber and a fluid output chamber in fluid communication therewith, an inlet in fluid communication with the receiving chamber and an outlet in fluid communication with the output chamber;

b) check valve means operatively associated with the fluid containing region for allowing fluid flow in a direction from the inlet through the outlet and blocking fluid flow in a direction from the outlet through the inlet;

c) electromagnet means carried by the housing and located external to the fluid containing region defined in the housing;

d) an armature positioned in the fluid containing region of the housing, the armature comprising a pole portion having a diameter for attraction to the electromagnet means and comprising a one piece plunger portion comprising a plurality of shaft portions and a head portion directly adjacent the pole portion and the head portion having a diameter substantially the same as the diameter of the pole portion, and the shaft portions having diameters and wherein the shaft portions are ordered such that the diameters of the shaft portions only increase in a direction toward the head portion and wherein the head portion diameter is greater than the diameters of the shaft portions, the one piece plunger portion and pole portion joined together and the pole portion located for magnetic attraction by the electromagnet means;

e) the armature being movably supported in the housing for movement from a rest position through a forward pumping stroke when the pole portion is attracted by the electromagnet to force fluid from the output chamber through the outlet and for movement in an opposite direction through a return stroke back to the rest position; and f) means defining a magnetic circuit including the electromagnet means and the armature and a gap between the pole portion of the armature and the electromagnet means for moving the armature toward the electromagnet means to close the gap in response to electrical energization of the electromagnet means.

2. The electromagnetic pump according to claim 1 wherein the shaft portions of the one piece plunger portion comprise a first shaft portion, a second shaft portion of greater diameter than the first shaft portion, a third shaft portion of greater diameter than the second shaft portion, and the head portion of greater diameter than the third shaft portion.

3. The electromagnetic pump according to claim 2 wherein the second shaft portion and third shaft portion meet at a shoulder.

4. The electromagnetic pump according to claim 1 wherein the one piece plunger portion comprises machined plunger stock.

5. The electromagnetic pump according to claim 1 further comprising:

a) a retainer element which defines a bore, the plunger portion of the armature is positioned through the bore in the retainer element and joined to the retainer element;

b) a retainer plate captured between the housing and an outer weld ring; and c) a main spring positioned between the retainer element and the retainer plate, the main spring for compressing and storing energy upon electrical energization of the electromagnet means as the armature is drawn to the electromagnetic means, and is for releasing energy and moving the armature to the rest position when electrical energization of the electromagnetic means ceases.

6. The electromagnetic pump according to claim 5 wherein the retainer element comprises an annular body for receiving the plunger portion and a lip, the main spring positioned between the lip of the annular body and the retainer plate.

7. The electromagnet pump according to claim 1 wherein the pole portion of the armature comprises a shell defining an interior loaded with a body of magnetic material for attraction by the electromagnetic means.

8. The electromagnetic pump according to claim 7 wherein the head portion defines a vacuum hole leading to the shell interior, so that when a vacuum is applied through the vacuum hole, the body of magnetic material is held against the head portion of the armature.

9. The electromagnet pump according to claim 8 wherein the shell is joined to the head portion by an inner weld ring.

10. The electromagnet pump according to claim 1 where the machined plunger portion comprises titanium, titanium alloys, biocompatible materials, and combinations thereof.

11. The electromagnetic pump according to claim 1 wherein one of the plunger shaft portions comprises an outer surface and the housing further comprises an adjacent housing inner surface that is adjacent to the outer surface of the one plunger shaft portion such that the armature is guided solely by cooperation between the outer surface of the one plunger shaft portion and the adjacent housing inner surface.

12. An electromagnetic pump comprising:

a) a housing defining an interior fluid containing region comprising a fluid receiving chamber and a fluid output chamber in fluid communication therewith, an inlet in fluid communication with the receiving chamber and an outlet in fluid communication with the output chamber;

b) check valve means operatively associated with the fluid containing region for allowing fluid flow in a direction from the inlet through the outlet and blocking fluid flow in a direction from the outlet through the inlet;

c) electromagnet means carried by the housing and located external to the fluid containing region defined in the housing;

d) an armature positioned in the fluid containing region of the housing, the armature comprising a pole portion and a plunger portion, the plunger portion comprises a first shaft portion, a second shaft portion comprising a greater diameter than the first shaft portion, a third shaft portion comprising a greater diameter than the second shaft portion, and a head portion comprising a greater diameter than the third shaft portion, the pole portion joined with the head portion and the pole portion located for magnetic attraction by the electromagnet means;

e) the armature being movably supported in the housing for movement from a rest position through a forward pumping stroke when attracted by the electromagnet means to force fluid from the output chamber through the outlet and for movement in an opposite direction through a return stroke back to the rest position; and f) means defining a magnetic circuit including the electromagnet means and the armature and a gap between the pole portion of the armature and the electromagnet means for moving the armature toward the electromagnet means to close the gap in response to electrical energization of the electromagnet means.

13. The electromagnetic pump according to claim 12 wherein the first shaft portion comprises an outer surface and the housing further comprises an adjacent housing inner surface that is adjacent to the outer surface of the first shaft portion such that the armature is guided solely by cooperation between the outer surface of the first shaft portion and the adjacent housing inner surface.

14. An electromagnetic pump comprising:
a) a housing defining a pump interior and an electromagnetic means carried by the housing,
b) an armature comprising a pole portion and a plunger portion, wherein the plunger portion is joined with the pole portion, and wherein in the rest position the armature is separated from the electromagnetic means by a gap space;
c) a retainer element defining a bore having a uniform diameter and comprising a lip, the plunger portion positioned in the bore of the retainer element and joined with the retainer element;
d) a main spring and a retainer plate, wherein the main spring is captured between the retainer plate and the lip of the retainer element and the main spring surrounds the plunger portion, and the retainer plate is captured between the housing and an outer weld ring joined to the housing; and
e) wherein in response to excitation of the electromagnetic means the armature moves through a forward stroke towards the electromagnetic means, compressing the main spring between the retainer element and the retainer plate closing the gap space, and wherein upon de-energizing the electromagnet means the main spring forces on the retainer element and moves the armature back to the rest position.

15. The electromagnetic pump according to claim 14 wherein the plunger portion comprises a first shaft portion, a second shaft portion of greater diameter than the first shaft portion, a third shaft portion of greater diameter than the second shaft portion, and a head portion of greater diameter than the third shaft portion, wherein the pole portion is joined to the head portion.

16. The electromagnetic pump according to claim 14 wherein the plunger further comprises shaft portions and wherein one of the plunger shaft portions comprises an outer surface and the housing further comprises an adjacent housing inner surface that is adjacent to the outer surface of the one plunger shaft portion such that the armature is guided solely by cooperation between the outer surface of the one plunger shaft portion and the adjacent housing inner surface.

17. A method of making an electromagnetic pump comprising the acts of:
a) providing a housing and defining an interior fluid containing region comprising a fluid receiving chamber and a fluid output chamber in fluid communication therewith, and providing an inlet in fluid communication with the receiving chamber and providing an outlet in fluid communication with the output chamber;
b) providing check valve means operatively associated with the fluid containing region for allowing fluid flow in a direction from the inlet through the outlet and blocking fluid flow in a direction from the outlet through the inlet;
c) providing electromagnet means carried by the housing and positioning the electromagnetic means external to the fluid containing region defined in the housing;
d) providing an armature pole portion having a diameter;
e) providing an armature plunger portion of a one-piece machined construction and providing the armature plunger portion with a plurality of shaft portions and a head portion directly adjacent the pole portion and the head portion having a diameter substantially the same as the diameter of the pole portion, and providing the shaft portions with diameters and ordering the shaft portions such that the diameters of the shaft portions only increase in a direction toward the head portion and providing the head portion with a head portion diameter greater than diameters of the shaft portions;
f) joining the armature plunger portion and armature pole portion and positioning the armature to locate the pole portion for magnetic attraction by the electromagnet means; and
g) defining a magnetic circuit including the electromagnet means and the armature and a gap between the pole portion of the armature for activating the electromagnet means for moving the armature from a rest position through a forward pumping stroke, closing the gap space, and forcing fluid from the output chamber through the outlet, and for de-energizing the electromagnetic means for moving the armature in an opposite direction through a return stroke back to the rest position.

18. The method according to claim 17 further comprising the acts of forming the plunger portion shaft portions into a first shaft portion, a second shaft portion of greater diameter than the first shaft portion, a third shaft portion of greater diameter than the second shaft portion, and the head portion of greater diameter than the third shaft portion.

19. The method according to claim 18 further comprising the acts of:
a) providing a retainer element and defining a bore therein, moving the plunger portion of the armature through the bore in the retainer element and joining the retainer element to the plunger portion;
b) positioning a retainer plate between the housing and an outer weld ring and joining the outer weld ring to the housing; and
c) positioning a main spring between the retainer element and the retainer plate for compressing the main spring upon activating the electromagnet means as the armature is drawn to the electromagnetic means, the main spring for storing energy and releasing energy to move the armature.

20. The electromagnetic pump according to claim 17 comprising the further acts of providing one of the plunger shaft portions with an outer surface and providing the housing with an adjacent housing inner surface that is adjacent to the outer surface of the one plunger shaft portion such that the guiding of the armature is solely by cooperation between the outer surface of the one plunger shaft portion and the adjacent housing inner surface.

21. A method assembling an electromagnetic pump comprising the acts of:
a) providing a housing;
b) defining an armature shaft recess comprising a first diameter in the housing
c) defining a main spring recess in the housing which comprises a second diameter greater than the first diameter;
d) defining a pole button recess in the housing which comprising a third diameter greater than the second diameter;
e) forming an armature into: a first shaft portion, a second shaft portion of greater diameter than the first shaft portion, a third shaft portion of greater diameter than the second shaft portion, a head portion of greater diameter than the third shaft portion;
f) providing a retainer element comprising an annular body defining a bore and comprising a surrounding lip extending from the annular body, and providing a retainer plate defining a central opening, and providing a main spring;

g) aligning the retainer plate central opening with the first shaft portion and moving the retainer plate until it contacts the head portion, moving the main spring over the first, second and third shaft portions, aligning the bore in the retainer element with the first shaft portion and moving the retainer element over the second shaft portion and joining the retainer element with the second shaft portion, and capturing the main spring between the retainer element and the retainer plate, h) inserting the armature in the armature shaft recess defined in the housing, first shaft portion first; and i) providing an electromagnet means for attracting the armature pole portion to move toward it in a forward stroke when activated and compress the main spring between the retainer element and the retainer plate, and wherein the main spring expands during the return stroke when the electromagnetic means deactivates.

22. The method according to claim 21 further comprising the acts of providing an outer weld ring with an outer weld ring lip, and positioning the outer weld ring in the pole button recess and welding it to the housing, and capturing the spring retainer between an adjacent housing area and outer weld ring lip.

23. The electromagnetic pump according to claim 21 wherein the first shaft portion comprises an outer surface and the housing further comprises an adjacent housing inner surface that is adjacent to the outer surface of the first shaft portion such that the armature is guided solely by cooperation between the outer surface of the first shaft portion and the adjacent housing inner surface.

24. An electromagnetic pump comprising:

a) a housing defining an interior fluid containing region comprising a fluid receiving chamber and a fluid output chamber in fluid communication therewith, an inlet in fluid communication with the receiving chamber and an outlet in fluid communication with the output chamber;

b) check valve means operatively associated with the fluid containing region for allowing fluid flow in a direction from the inlet through the outlet and blocking fluid flow in a direction from the outlet through the inlet;

c) electromagnet means carried by the housing and located external to the fluid containing region defined in the housing;

d) an armature positioned in the fluid containing region of the housing, the armature comprising a pole portion for attraction to the electromagnet means and comprising a one piece plunger portion comprising shaft portions of increasing diameters and a head portion comprising a diameter greater than the shaft portions, the one piece plunger portion and pole portion joined together and the pole portion located for magnetic attraction by the electromagnet means;

e) the armature being movably supported in the housing for movement from a rest position through a forward pumping stroke when the pole portion is attracted by the electromagnet to force fluid from the output chamber through the outlet and for movement in an opposite direction through a return stroke back to the rest position;

f) means defining a magnetic circuit including the electromagnet means and the armature and a gap between the pole portion of the armature and the electromagnet means for moving the armature toward the electromagnet means to close the gap in response to electrical energization of the electromagnet means;

g) wherein the one piece plunger portion comprises a first shaft portion, a second shaft portion of greater diameter than the first shaft portion, a third shaft portion of greater diameter than the second shaft portion, and a head portion of greater diameter than the third shaft portion; and h) wherein the second shaft portion and third shaft portion meet at a shoulder.

25. The electromagnetic pump according to claim 24 further comprising a retainer element defining a bore through which the second shaft portion passes, the retainer element joined with the second shaft portion at about the shoulder, and a retainer plate which defines a central opening through which the third shaft portion passes the retainer plate positioned between the housing and an outer weld ring, and a main spring positioned between the retainer element and the retainer plate, the main spring for compressing and storing energy during the forward pumping stroke of the armature and for expanding and releasing energy and moving the armature to a rest position during the return stroke.

26. The electromagnetic pump according to claim 25 wherein the armature pole portion comprises a body of magnetic material for attraction to the electromagnet means and an inner weld ring joins the pole portion to the one piece plunger portion, and upon excitation of the electromagnetic means the pole portion of the armature responds and is drawn towards the electromagnetic means and compresses the main spring.

27. The electromagnetic pump according to claim 24 wherein the first shaft portion comprises an outer surface and the housing further comprises an adjacent housing inner surface that is adjacent to the outer surface of the first shaft portion such that the armature is guided solely by cooperation between the outer surface of the first shaft portion and the adjacent housing inner surface.

28. An electromagnetic pump comprising:

a) a housing defining a pump interior and an electromagnetic means carried by the housing, b) an armature comprising a pole portion and a plunger portion, wherein the plunger portion is joined with the pole portion, and wherein in the rest position the armature is separated from the electromagnetic means by a gap space;

c) a retainer element defining a bore and comprising a lip, the plunger portion positioned in the bore of the retainer element and joined with the retainer element;

d) a main spring and a retainer plate, wherein the main spring is captured between the retainer plate and the lip of the retainer element and the main spring surrounds the plunger portion, and the retainer plate is captured between the housing and an outer weld ring joined to the housing;

e) wherein in response to excitation of the electromagnetic means the armature moves through a forward stroke towards the electromagnetic means, compressing the main spring between the retainer element and the retainer plate closing the gap space, and wherein upon de-energizing the electromagnet means the main spring forces on the retainer element and moves the armature back to the rest position; and f) wherein the plunger portion comprises a first shaft portion, a second shaft portion of greater diameter than the first shaft portion, a third shaft portion of greater diameter than the second shaft portion, and a head portion of greater diameter than the third shaft portion, wherein the pole portion is joined to the head portion.

29. The electromagnetic pump according to claim 28 herein the second shaft portion and third shaft portion meet at a shoulder and the retainer element is joined to the second shaft portion at about the shoulder.

30. The electromagnetic pump according to claim 28 wherein the plunger portion is machined from a piece of plunger stock.

31. The electromagnetic pump according to claim 28 wherein the plunger portion is machined from a single piece of plunger stock and comprises titanium, titanium alloys, metal and combinations thereof.

32. A low power electromagnetic pump comprising:
   a) a housing that defines an interior fluid containing region comprising a fluid receiving chamber and a fluid output chamber in fluid communication therewith, an inlet in fluid communication with the receiving chamber and an outlet in fluid communication with the output chamber, and the housing further comprising a housing inner surface that defines an armature plunger shaft chamber, the armature plunger shaft chamber being in fluid communication with the fluid receiving chamber and fluid output chamber;
   b) check valve means operatively associated with the fluid containing region used for allowing fluid flow in a direction from the inlet through the outlet and blocking fluid flow in a direction from the outlet through the inlet;
   c) electromagnet means carried by the housing and located external to the fluid containing region defined in the housing;
   d) an armature positioned in the housing and having a pole portion for attraction to the electromagnet means and a plunger portion, the plunger portion comprising a shaft section having an outer surface and positioned in the armature plunger shaft chamber;
   e) wherein when a length of the plunger shaft section is increased a set amount, a distance between the housing inner surface and the outer surface of the plunger shaft section is increased until the distance equals the set amount raised to the one third power;
   f) wherein the armature is movably supported in the housing and guided solely by cooperation between the plunger shaft section and the housing inner surface which defines the armature plunger shaft chamber for movement from a rest position through a forward pumping stroke when the pole portion is attracted by the electromagnet to force fluid from the output chamber through the outlet and for movement in an opposite direction through a return stroke back to the rest position; and
   g) means defining a magnetic circuit including the electromagnet means and the armature and a gap between the pole portion of the armature and the electromagnet means for moving the armature toward the electromagnet means to close the gap in response to electrical energization of the electromagnet means.

33. A method of making a low electromagnetic pump comprising the step of:
   a) providing a housing and defining an interior fluid containing region comprising a fluid receiving chamber and a fluid output chamber in fluid communication therewith, providing an inlet in fluid communication with the receiving chamber and providing an outlet in fluid communication with the output chamber, and providing the housing with a housing inner surface and defining an armature plunger shaft chamber in the housing, the armature plunger shaft chamber being in fluid communication with the fluid receiving chamber and fluid output chamber;
   b) providing check valve means operatively associated with the fluid containing region used for allowing fluid flow in a direction from the inlet through the outlet and blocking fluid flow in a direction from the outlet through the inlet;
   c) providing electromagnet means carried by the housing and locating the electromagnetic means external to the fluid containing region defined in the housing;
   d) providing an armature and positioning the armature in the in the housing and providing the armature with a pole portion used for attraction to the electromagnet means and a plunger portion, providing the plunger portion with a shaft section having an outer surface and positioning the plunger portion in the armature plunger shaft chamber;
   e) providing the plunger shaft section with a length and increasing the length of the plunger first shaft section a set amount and providing a distance between the housing inner surface and the outer surface of the plunger shaft section and increasing the distance between the housing inner surface and the outer surface of the plunger shaft section until the distance equals the set amount raised to the one third power;
   f) movably supporting the armature in the housing and guiding the armature solely by cooperation between the plunger shaft section and the housing inner surface which defines the armature plunger shaft chamber for moving the armature from a rest position through a forward pumping stroke when the pole portion is attracted by the electromagnet to force fluid from the output chamber through the outlet and for movement in an opposite direction through a return stroke back to the rest position; and
   g) providing means defining a magnetic circuit including the electromagnet means and the armature and providing a gap between the pole portion of the armature and the electromagnet means for moving the armature toward the electromagnet means to close the gap in response to electrically energizing the electromagnet means.

* * * * *